United States Patent [19]

Lomick

[11] Patent Number: 5,279,557
[45] Date of Patent: Jan. 18, 1994

[54] MULTIPLE CHAMBER IV DELIVERY DEVICE

[76] Inventor: Joe B. Lomick, 120 Kentington Rd., Durham, N.C. 27713

[21] Appl. No.: 65,743

[22] Filed: May 24, 1993

[51] Int. Cl.$^5$ ............................................. A61M 5/14
[52] U.S. Cl. ....................................... 604/80; 604/254
[58] Field of Search .................. 604/80, 81, 82, 83, 604/84, 254, 247, 246, 245

[56] References Cited

U.S. PATENT DOCUMENTS

| | | | |
|---|---|---|---|
| 3,216,419 | 11/1965 | Scislowicz | 604/254 |
| 3,227,173 | 1/1966 | Bernstein | 604/254 |
| 4,114,617 | 9/1978 | Turner et al. | 604/80 |

*Primary Examiner*—John D. Yasko
*Attorney, Agent, or Firm*—Charles Edison Smith

[57] ABSTRACT

A multiple chamber IV manifold delivery device for controlling infusion of blood, medical drugs or other solutions to a medical patient. The manifold includes a transparent housing defining a set of drip chambers that communicate with a Y-site fluid reservoir that delivers fluid to a conduit line leading to a medical patient. The Y-site reservoir is provided with a flotation check valve. The manifold delivery device is operable to control the order of delivery of at least two fluid solutions from separate supply chambers to a medical patient. The flotation check valve is used to maintain one supply chamber in a sealed condition while another chamber supplies fluid to be administered to a patient. The IV manifold device is provided with exit and entry ports to enable the device to be coupled together with at least two other similarly constructed apparatus to thereby increase the time period for administering drugs of fluids to a medical patient.

9 Claims, 1 Drawing Sheet

MULTIPLE CHAMBER IV DELIVERY DEVICE

BACKGROUND OF THE INVENTION

1. Field of the Invention

This invention relates in general to an apparatus for intravenous administration of blood, medication drugs and/or other fluid solutions to medical patients. More specifically, the invention relates to an improved apparatus for delivering blood or an intravenous fluid typically, a solution such as saline, glucose or electrolyte to medical patients via a multiple chamber manifold device, automatically without the aid of manual or electrical switches.

2. Prior Art

Infusion delivery systems for administering blood or fluids to a medical patient from more than one solution source have been described in the prior art. A common system shown in the prior art features gravity flow and manually adjustable tubing clamps or pinch valves. A variety of valves and junctions may be used to control fluid delivery at a desired rate and sequence. Examples of such systems are described in U.S. Pat. Nos. 3,886,937; 4,034,754; 4,14,617; 4,219,022; 4,223,695; 4,236,515; 4,237,879; 4,237,880; 4,250,879; 4,252,116; 4,256,104; 4,456,105; 4,258,712; 5,200,090; and RE 33,021. Dual delivery systems relying on electronic flow control means are described in U.S. Pat. No. 4,094,318, for example.

There is a need for a drug IV infusion manifold delivery system for providing extended administration of medical drugs or solutions that do not require manipulation or intervention by hand or manual switching operation.

There is a further need for a IV manifold delivery system that reduces the need to transfer or switch from an empty sterile container to another supply fluid container.

There is still a further need drug IV manifold delivery systems operable to control the order of delivery of two separate fluid solutions to a medical patient.

SUMMARY OF THE INVENTION

One object of the present invention is to permit infusion of medical drugs or other solutions through the use of a dual chamber manifold delivery device that is controlled by a flotation check valve.

Another object of the invention is to operate an IV manifold delivery system to extend the time period of administering fluid solutions to a patient without need for hand manipulation or manual or electric switching mechanisms.

A further object of the invention is to selectively couple IV manifold delivery systems together and administer increased amounts of fluid solutions to a patient.

Still another object of the invention is to operate a flotation check value to control the order of delivery of fluid solutions from exit channels of separate drip chambers.

Other objects and advantages of the present invention will become readily apparent to those skilled in this art from the following detailed description, wherein there is shown and described only the preferred embodiment or the invention, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not restrictive.

DESCRIPTION OF THE PREFERRED EMBODIMENT

Figures 6, 7:
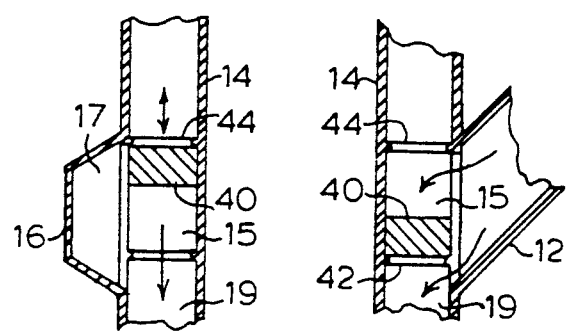
FIG. 6 is a fragmentary cross-sectional view of the multiple chamber IV infusion apparatus of the invention along the axis 6—6 of FIG. 1 illustrating the flotation check valve according to the invention.
FIG. 7 is a fragmentary cross-sectional view of the multiple chamber IV infusion apparatus of the invention along the axis 7—7 of FIG. 2 illustrating the flotation check valve and control of the order of delivery of fluids from channels of a set of drip chambers.

As shown diagrammatically generally in FIGS. 1-5, and more particularly in FIGS. 6 and 7, the multiple chamber IV manifold delivery device 10 of the present invention operates to permit infusion of blood, medical drugs or other solutions to a medical patient through the use of a dual drip chambers 12 and 14 that deliver fluid from exit channels to a Y-site that contains a flotation check valve 40.

The IV manifold delivery apparatus 10, formed of a transparent housing, enables a plurality of containers that contain, typically example, 250, 500 or 1,000 milliliters of intravenous fluids vacuum packed in sterile glass or plastic bags attached to it to be delivered to a medical patient. The IV manifold delivery apparatus 10 can also be used to deliver fluid contents of even smaller size containers, for example piggyback IV bags. The fluid containers are mounted at the same gravity level on fluid vents 24 and 26 and secured by clamps 20 and 22 respectively. The fluid vent 26 is routed through clamp 22 and through an opening leading into the first drip chamber 12 so that fluid is delivered from a fluid container positioned on IV standard or pole directly into a first drip chamber 12. The fluid vent 24 is routed through clamp 20 and through an opening leading into the second drip chamber 14 so that fluid is delivered from a fluid container positioned on an IV standard or pole directly into a second drip chamber 14.

Referring now more particularly to FIGS. 6 and 7, the exit branches or flow channels from the first drip chamber 12 and second drip chamber 14 are connected by a Y-site to form a fluid reservoir 15 at the Y-site. The first drip chamber 12 intersects the second drip chamber 14 at the Y-site reservoir 15 at an angle of between 40-45 degrees. The second drip chamber 14 contains an access port or membrane 28 that allows a drug to be injected with a needle and syringe into the chamber to permit the patient to receive the medication more quickly than had the drug been mixed with entire amount of solution in the container.

Leading from the Y-site reservoir 15 is an exit flow channel 19 to permit the expulsion of the fluid contents into a conduit attachment 35 at the bottom of the IV manifold delivery device 10. The conduit attachment 35 may lead to the medical patient recipient.

Referring now generally to FIGS. 1–5 and more specifically to FIGS. 6 and 7, there is illustrated the manner in which the IV manifold delivery device 10 is operated to control the order of delivery of at least two fluid solutions to a medical patient. Although a set of fluid containers are mounted at the same approximate elevation level at fluid vents 24 and 26, the order of delivery of fluids contents from the two fluid sources attached to fluid vents 24 and 26, into the Y-site reservoir 15 and through the exit flow channel 19 to the patient can be controlled. Medical personnel may simply elect to start the release or discharge of fluid solution positioned on a standard or IV pole above the fluid vent 26 first. The fluid contents expelled from the first drip chamber 12 will thus, empty first into the Y-site reservoir 15, then to the exit flow channel 19, and will enter the patient's vein before, and without significant mixing with the drug or fluid solution contents from the second drip chamber 14. As shown by FIGS. 6 and 7, fluid solution delivered into first drip chamber 12 will be expelled through an exit flow channel into the Y-site reservoir 15. Fluid solution entering into the Y-site reservoir 15 will initially contact the top surface of flotation check valve 40, but the fluid will escape over the top surface to the exit flow channel 19 beneath the flotation check valve 40. The flotation check valve 40, which typically may be constructed of any suitable material that is capable of floating. This construction will permit the fluid solution to pass over the surface and under the flotation check valve 40, and also seep between the edge of the flotation check valve 40 and the IV manifold apparatus housing wall into the Y-site reservoir 15. After a period the flotation check valve 40 will begin to rise upward in the direction of the second drip chamber 14, and eventually will allow virtually unimpeded passage of fluid solution flowing from the first drip chamber 10. When the fluid contents at the Y-site reservoir 15 rises to a predetermined critical level at the upper interior stop 44, the exit flow channel from the second drip chamber 14 will automatically self-seal, thus preventing seepage or any fluid from otherwise being expelled into the Y-site reservoir 15. This self-sealing condition is achieved and maintained so long as the flotation check valve 40 is positioned in a certain location relative to the opening leading from the exit flow channel of the first drip chamber 12. After the flotation check valve 40 has established a self-sealing condition at upper interior stop 44, fluid solution maintained in, released or delivered to second drip chamber 14 will remain in the chamber until the fluid solution delivered to the first drip chamber 12 empties and no longer flows sufficiently to maintain the check valve 40 in the self-seal condition.

After the fluid solution from the first drip chamber 12 is empty, when fluid is released or delivered int the second drip chamber 14, flotation check valve 40 will move in a downward direction toward the bottom of the Y-site reservoir 15. When the fluid contents in the second drip chamber 14 causes the flotation check valve to fall below a certain critical level, fluid will quickly pass into the reservoir overflow 16, and therefrom underneath the flotation check valve 40 and into the Y-site reservoir 15 and to the exit flow channel 19. Eventually, the flotation check valve will come to rest at lower interior stop 42

Figure 1:
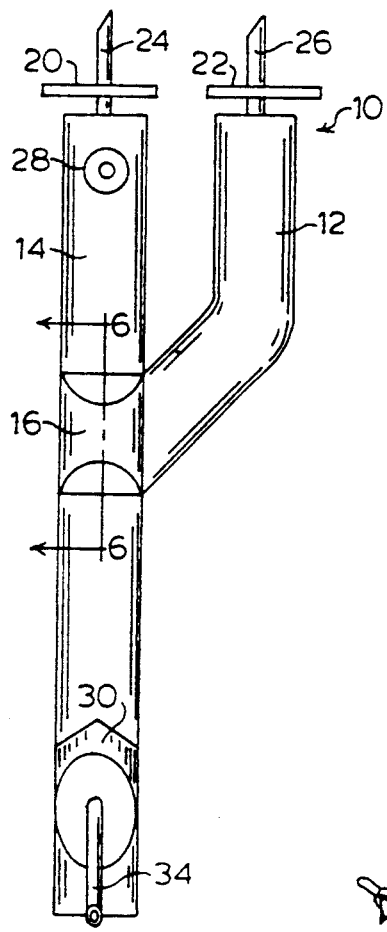
FIG. 1 is a front elevation view of the multiple chamber IV infusion apparatus for controlling the operation and order of delivery of blood or fluid solutions to medical patients.
Figure 2:
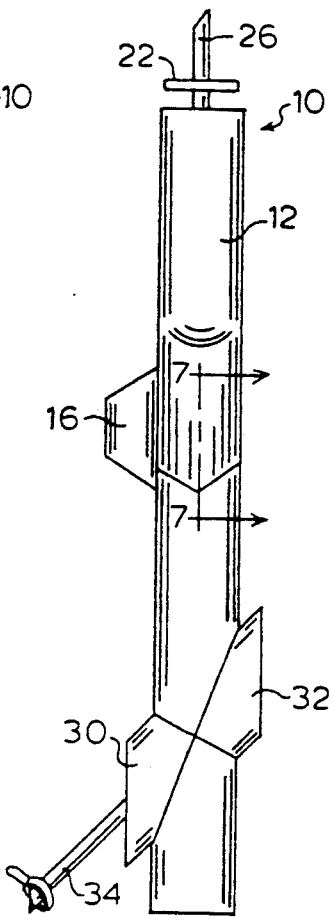
FIG. 2 is a right side view elevation of the multiple chamber IV infusion apparatus of FIG. 1 according to the invention.
Figure 3:
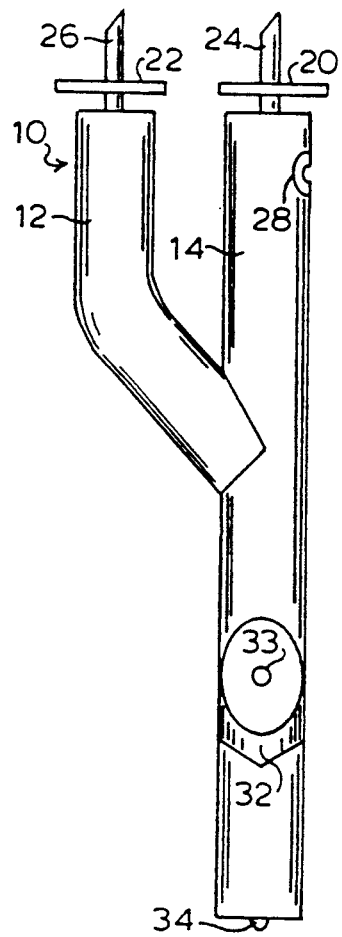
FIG. 3 is a rear elevation view of the multiple chamber IV infusion apparatus of FIG. 1 according to the invention.
Figure 4:
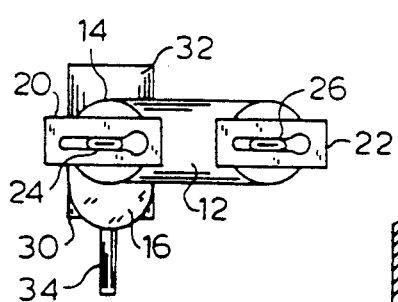
FIG. 4 is a top view of the multiple chamber IV infusion apparatus shown in FIG. 1 according to the invention.
Figure 5:
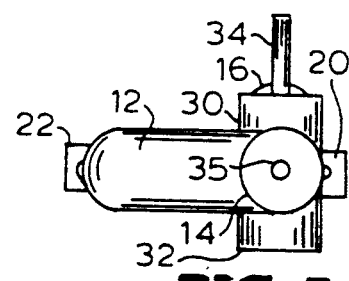
FIG. 5 is a bottom view of the multiple chamber IV infusion apparatus of FIG. 1 according to the invention.

The IV manifold delivery device 10 is constructed to allow medical personnel to significantly increase the amount of fluid solution administered to a patient by providing continuous flow of fluid over extended time periods without need for hand manipulation or manual or electric switching mechanisms. Referring particularly to FIGS. 1–3, the IV manifold device 10 is constructed to be coupled together with at least two other similarly constructed apparatus. An exit or outlet port 30 positioned near the bottom region of the IV manifold device 10 is adapted to receive and attach one end of line 34 that leads to an entrance or inlet port of another similarly constructed apparatus. The other similarly constructed apparatus may, in turn, couple its outlet port to the inlet port of yet another similarly constructed apparatus. When the IV line 35 is clamped shut, line 34 will deliver fluid solutions from outlet port 30 and into an inlet port of another apparatus, or alternatively, line 34 may lead directly to the medical patient.

The IV manifold device also is adapted to receive fluid solution from another similarly constructed apparatus. An entrance or inlet port 32 positioned near the bottom region of the IV manifold device, opposite but at a slightly higher elevation than the outlet port 30, is adapted to receive and connect one end of a line from the outlet port of a similarly constructed apparatus. The other similarly constructed apparatus may, in turn, receive and connect to a line from the outlet port of yet another similarly constructed apparatus.

What is claimed as my invention is as follows:

1. In a multiple chamber IV manifold formed of a transparent housing for controlling delivery of blood, medical drugs and/or other fluid solutions to a medical patient comprising a first drip chamber positioned to receive a first fluid source, said first drip chamber having a first fluid vent mounted to receive said first fluid source, a second drip chamber positioned to receive a second fluid source, said second drip chamber having a second fluid vent mounted to receive said second fluid source at the same gravity level as said first fluid vent, said first drip chamber and said second drip chamber having exit flow channels that deliver fluid to a Y-site reservoir, said first drip chamber intersects said second drip chamber at the Y-site reservoir at an angle of between 40–45 degrees and a flotation check valve contained within said Y-site reservoir, said first fluid solution delivered into said first drip chamber is delivered or expelled through the exit channel of said first drip chamber into the Y-site reservoir prior to and in advance of delivery of expulsion of said second fluid solution into said second drip chamber, said first fluid solution entering into said Y-site reservoir will initially contact the top surface of said flotation check valve and therefrom said first fluid solution will escape over the top surface to the exit flow channel beneath the flotation check valve.

2. The apparatus according to claim 1, wherein said flotation check valve is constructed to permit said first fluid solution to pass over the surface and under said flotation check valve and seep between the edge of said flotation check valve and said the IV manifold apparatus housing wall at said Y-site reservoir, whereby after a period said flotation check valve will begin to rise upward in the direction of said second drip chamber and when a critical elevation level is obtained, allow virtually unimpeded passage of said first fluid solution flowing from said first drip chamber.

3. The apparatus according to claim 2, wherein said first fluid solution in said Y-site reservoir rises to a predetermined critical level at a stop whereby the exit flow channel from said second drip chamber will automatically self-seal, preventing seepage, or any fluid from otherwise being expelled into said Y-site reservoir.

4. The apparatus according to claim 3, wherein said self-sealing condition is achieved and maintained so long as said flotation check valve is positioned in a certain location relative to the opening leading from the exit flow channel of said first drip chamber.

5. The apparatus according to claim 4, wherein when said flotation check valve establishes said self-sealing condition at said stop said second fluid solution maintained in, released or delivered to said second drip chamber will remain in said second drip chamber until said first fluid solution delivered to said first drip chamber empties and no longer flows sufficiently to maintain the flotation check valve in said self-seal condition.

6. The apparatus according to claim 5, wherein after said first fluid solution from said first drip chamber is empty, said second fluid solution is released or delivered into said second drip chamber to thereby cause said flotation check valve to move in a downward direction toward the bottom of said Y-site reservoir.

7. The apparatus according to claim 6, wherein when said second fluid solution in said second drip chamber causes said flotation check valve to fall below a certain critical level, fluid will quickly pass into the reservoir overflow, and therefrom underneath said flotation check valve and into the Y-site exit flow channel.

8. The apparatus according to claim 7, wherein said IV manifold device contains an outlet port positioned near the bottom region of said IV manifold device, said outlet port is adapted to receive and attach one end of a conduit line connected to an entrance or inlet port of another similarly constructed IV manifold device.

9. The apparatus according to claim 8, wherein said IV manifold device contains an inlet port near the bottom region of said IV manifold device, opposite but at a slightly higher elevation than said outlet port, said inlet port is adapted to receive and connect one end of a conduit line from the outlet port of another similarly constructed IV manifold device.

* * * * *